United States Patent [19]

Karlsoen

[11] 4,147,500

[45] Apr. 3, 1979

[54] SYSTEM FOR CONTINUOUS ANALYSIS OF GASSES

[75] Inventor: Harald Karlsoen, Siggerud, Norway

[73] Assignee: Elkem-Spigerverket A/S, Oslo, Norway

[21] Appl. No.: 811,826

[22] Filed: Jun. 30, 1977

[30] Foreign Application Priority Data

Jun. 30, 1976 [NO] Norway ................................. 762263

[51] Int. Cl.² ............................................. F23J 15/00
[52] U.S. Cl. .......................................... 432/2; 432/72; 236/15 E; 73/421.5 A; 266/80; 55/270; 431/76
[58] Field of Search ..................... 432/72, 2, 4, 75, 50, 432/37, 38, 48, 66, 67, 1; 62/5; 236/15 E; 73/421.5 A; 266/80, 99; 55/269, 270; 431/76

[56] References Cited

U.S. PATENT DOCUMENTS

| | | | |
|---|---|---|---|
| 2,489,893 | 11/1949 | Johnson | 73/421.5 A |
| 2,550,933 | 5/1951 | McEvoy | 73/421.5 A |
| 2,685,205 | 8/1954 | Bannard | 73/421.5 A |
| 3,437,321 | 4/1969 | Wilkinson | 432/72 |
| 3,495,463 | 2/1970 | Howell | 73/421.5 A |
| 3,595,544 | 7/1971 | Curtis | 432/37 |
| 3,680,388 | 8/1972 | Critchley et al. | 73/421.5 A |
| 3,942,330 | 3/1976 | Schroder | 62/5 |
| 4,026,120 | 5/1977 | Tallant | 62/5 |

OTHER PUBLICATIONS

IBM Technical Disclosure Bulletin, vol. 18, No. 2, 7/1975, pp. 428-429.

Primary Examiner—Henry C. Yuen
Attorney, Agent, or Firm—Eyre, Mann, Lucas & Just

[57] ABSTRACT

A system for the continuous analysis of furnace gasses for carbon dioxide and oxygen levels is disclosed. Materials which would be detrimental to the measuring instruments are removed before the gasses reach the measuring instruments. In particular, moisture content is removed by condensation at temperatures near freezing whereafter the gas is permitted to continuously warm up as it goes through the measuring instruments so that no condensation takes place in the measuring instruments.

21 Claims, 1 Drawing Figure

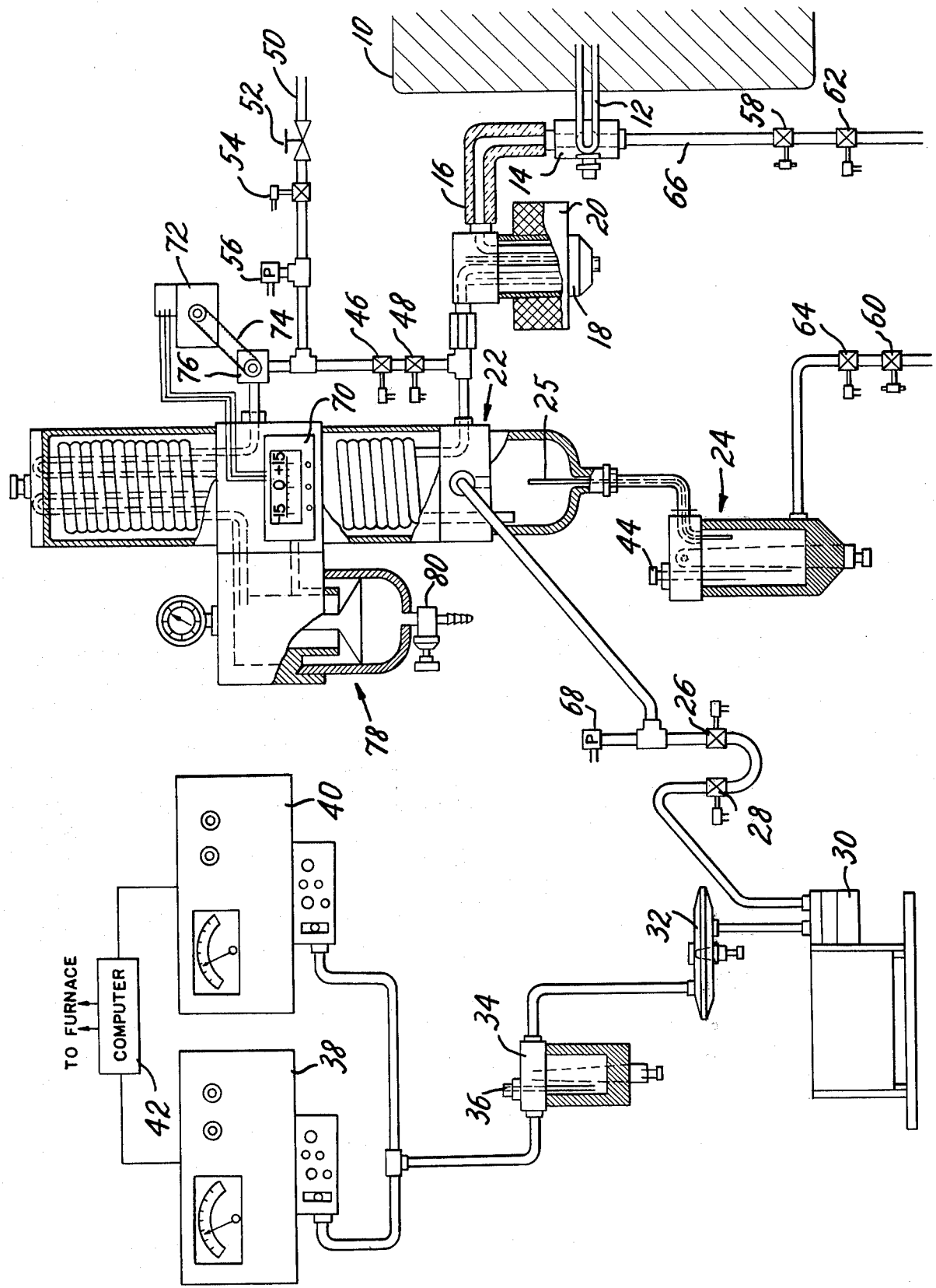

SYSTEM FOR CONTINUOUS ANALYSIS OF GASSES

The present invention relates to a system for the continuous measurement of gasses from furnaces so that appropriate adjustments to the furnace system can be made.

It is well-known that furnace gasses tell a considerable amount about the functioning of the furnace. In particular, the levels of oxygen and carbon dioxide are important. These levels are frequently measured so that adjustments to the furnace and especially adjustments in the air/fuel ratio can be made. With modern day computer systems, it is highly valuable to be able to continuously monitor the oxygen and carbon dioxide levels in the furnace gasses so that continuous adjustments can be made to the furnace to obtain and maintain the most effecient operation.

The problem which is encountered in making continuous measurements is that the water in the furnace gasses and the particulate matter suspended in the furnace gasses are highly detrimental to the measuring instruments. More particularly, the water will frequently combine with sulfur dioxide to form the highly caustic sulfuric acid.

There are, of course, ways for removing water content and particulate matter from gasses. However, unless a system is available for the continuous removal of these materials so that the gasses can be continuously monitored, it is not possible to obtain the most effecient operation of the furnace.

In accordance with the present invention there is taught a system for the continuous removal of moisture and particulate matter from furnace gasses whereby the gas may then be analyzed for components such as oxygen and/or carbon dioxide in a continuous manner and adjustments to the furnace operation can be continuously made. The system has particular application where the output from the measuring instruments is connected to a computer which continuously analyzes the data and continuously adjusts furnace operation according thereto.

These and other aspects of the present invention may be more fully understood by reference to the accompanying FIGURE.

The FIGURE shows the preferred embodiment of an apparatus according to the present invention.

Referring to the figure, gasses are removed from a furnace 10 through pipe 12. The gasses first go through an inspection device 14 whereafter they travel through an insulated pipe 16 to a ceramic heating filter 18. The ceramic heating filter 18 is heated, suitably by means of an electronic bulb 20. The ceramic heating filter removes substantially all of the particulate matter from the furnace gasses. After passing through the ceramic heat filter, the gasses pass to a cooler, suitably a vortex cooler 22 as shown. In the cooler the gas is cooled to near the freezing point of water, i.e. to about 1°-2° C. During this cooling, the moisture in the gas will condense. The water will thus separate from the gas and will collect in the lower part of the cooler from which it is conducted to a container 24. In order to maintain a closed system and avoid the need for venting to the atmosphere, a capillary tube 25 is provided between the water collection container 24 and the vortex cooler 22 for the passage of air as it is displaced by the rising water level. In the vortex cooler, the gas is cooled according to the adiabatic equilibrium principle for the expansion of air. From the cooler 22, the gas passes through valves 26 and 28 to pump 30 which pumps the gas through a filter 32, suitably a paper filter, and then through a water separator 34. The water separator 34 is primarily a protection device. It is provided with a water level sensor 36. If enough water is removed from the gasses by the water separator 34 to reach the water level sensor 36, this is an indication that the earlier water separator has for some reason malfunctioned. At this point, the sensor 36 will immediately shut down the system so that no gasses reach measuring instruments 38 and 40 and damage them.

Presuming, however, that all has gone well and level indicator 36 has not been activated to shut down the system, the gasses pass from water separator 34 to measuring instruments 38 and 40. Two such measuring instruments are shown and they are preferably used to monitor oxygen and carbon dioxide levels. Obviously, only one of the instruments need be employed if desired and, obviously, additional instruments could also be employed if desired. The measured data from the instruments 38 and 40 is preferably fed to a computer 42 which continuously monitors the data and adjusts furnace operating conditions accordingly.

One of the important features of the present invention is that the moisture is removed by cooling rather than by other means such as a desiccant or the like. The importance of cooling is that after the gas leaves the vortex cooler 22 it continuously warms up as it passes through the line to the measuring instruments 38 and 40. This heating is effected by the warmness of the ambient temperature and the heat of operation of components 26, 28 and 30. Additional heat mey also be supplied to effect a greater rise in temperature if desired. Because the gas is continuously heating up, there is virtually no tendency for water to condense out of the gas stream as it is passing through the measuring instruments 38 and 40. Such an advantageous result could not be achieved if water were removed by means other than cooling and condensation. Because the moisture is removed by condensing it to the liquid form, the container 24 for collecting the water from the vortex cooler 22 can also function as an indicator for flushing of the system. More particularly, a water level sensor 44 can be employed to indicate the water level in container 24. When the water level reaches a preselected level, the system can be flushed to clean it. The preselected level for start of the cleaning operation will be largely dependent upon the quickness with which ceramic heat filter 18 becomes clogged. This is determined largely by a trial and error system.

When the water reaches the preselected level in the water container 24 and the water level sensor 44 is activated, the main gas stream is shut off and flushing gas is introduced into the system. More particularly, valves 26 and 28 are closed to prevent any further flow to the measuring instruments 38 and 40. Thereafter magnetic valves 46 and 48 are opened to permit the ingress of compressed air from line 50. The compressed air passes through a hand valve 52, a magnetic valve 54 and a pressure controller 56. At the same time, throttle valves 58 and 60 and magnetic valves 62 and 64 are opened. The compressed air thus blows the collected moisture out of container 24 and at the same time it cleans ceramic heat filter 18 by reverse flushing thereof. Furthermore, any moisture which has collected in line 66 is blown out of the system.

Water level indicator 44 preferably senses not only an upper limit of water level but also a lower limit. Thus, when the lower limit is reached this can be used an as indicator to automatically shut off the flushing system and resume monitoring of the gas. The advantage to leaving some water in the container 24 is that it forms a water seal to prevent air from entering the system. The duration of the purge cycle can be controlled by means of the throttle valves 58 and 60. Since the purge system will not shut off until the water level reaches the preselected minimum level, control of the rapidity with which the water reaches that minimum level will obviously also control the duration of the clean cycle. Similarly, adjustment of throttle valve 58 will affect the amount of pressure used to back flush filter 18 and will simultaneously control the amount of pressure fed to water container 24. As with the frequency of cleaning, the duration of the purge cycle is also determined primarily by trial and error depending upon the degree of particulate matter generated by the particular fuel employed and the degree of difficulty of back flushing it out of the particulate filter 18. When the water level has reached the preselected minimum level in the container 24 and the purge system is to be shut off, magnetic valves 46 and 48 are closed. When pressure controller 68 is at 0-pressure, valves 26 and 28 are reopened and the pump 30 is also reactivated. The system is now fully operative again. Since the purge cycle is comparatively short and since it can be automatically activated and deactivated, the system can be an automatic and essentially continuous system.

As can be seen from the figure, the compressed air introduced through line 50 also serves as the refrigerant for the vortex cooler 22. Control of temperature is very important since too high a temperature will not cause enough condensation and removal of water and too low a temperature can result in freezing of the water whereby it will not be removed, it is highly advantageous to have close control of temperature in the vortex cooler. Furthermore, since the temperature of the gasses coming from the furnace 10 will vary considerably, especially because of changes in ambient air temperature between day time and night time operation, the temperature inside the air vortex cooler should be constantly monitored and adjusted. For this purpose there is suitably employed a resistance type thermocouple 70 which constantly monitors internal temperatures and sends a signal corresponding to internal temperatures to a balance motor 72 which, through chain 74, governs a reduction valve 76 for controlling the amount of compressed air introduced to the vortex cooler. The compressed air used for cooling is exhausted from vortex cooler 22 through apparatus 78 which is provided with a petcock 80 for removal of water and solid contaminants.

It will be noted that a number of safety devices have been built into this system. One of them, water separator 34 was previously discussed. A second obvious one is the use of dual magnetic valve systems 26, 28 and 46, 48 so that failure of one does not result in a breakdown of the system. A further safety device is pressure controller 56 which determines whether or not there is sufficient pressure in the equipment to operate. If the pressure falls too low or fails completely, pressure cooler 56 shuts down valve 54 and shuts down the entire system so that the measuring instruments do not become damaged. Hand valve 52 is normally maintained in the open position but is included for manual operation if such should become necessary.

While it is possible to use the present invention with any type of furnace, it will be appreciated that the most benefit will be obtained when the present invention is used with industrial furnaces.

It will be understood that the claims are intended to cover all changes and modifications of the preferred embodiments of the invention, herein chosen for the purpose of illustration, which do not constitute departures from the spirit and scope of the invention.

What is claimed is:

1. An apparatus for cleaning of gas from a furnace prior to the gas passing through at least one measuring instrument for analysis thereof, said apparatus including filter means for removing particulate matter and cooling means for removing moisture, said cooling means cooling the furnace gas to a temperature approaching the freezing point of water whereby moisture in the furnace gas is condensed and removed from the furnace gas and wherein the water condensed in the cooling means is removed to a separate container, said separate container includes a water level sensor which is activated upon the water level reaching a predetermined height in said separate container, and wherein activation of the water level indicator automatically generates a signal operative to close valve means which shut off the furnace gas flow to the measuring instruments and open other valve means to permit the supply of a pressurized gas to said separate container and to said filter means to thereby reduce the water level in said separate container and to clean said filter means by reverse flushing thereof.

2. The apparatus of claim 1 wherein the filter means is a heated filter.

3. The apparatus of claim 2 wherein the heated filter is a heated ceramic filter.

4. The apparatus of claim 1 further including means for controlling the rate of reduction of water level in said separate container.

5. The apparatus of claim 1 wherein said separate container further includes a low level water indicator which, when activated, generates a signal operative to close said other valve means to shut off the supply of pressurized gas to said separate container and said filter means and to reopen said valve means to again permit furnace gas flow to said measuring instruments.

6. The apparatus of claim 1 wherein the cooling means is a vortex cooler.

7. The apparatus of claim 6 wherein the coolant for the vortex cooler is compressed air and the same supply of compressed air is used as the said pressurized gas.

8. The apparatus of claim 1 further including means for monitoring the temperature in said cooling means and adjusting the temperature in said cooling means to a predetermined level approaching the freezing point of water.

9. The apparatus of claim 8 wherein the said means for monitoring is a thermocouple and wherein adjustments in temperature are made by adjusting the supply of coolant fed to the cooling means.

10. An apparatus for cleaning of gas from a furnace prior to the gas passing through at least one measuring instrument for analysis thereof, said apparatus including filter means for removing particulate matter and cooling means for removing moisture, said cooling means cooling the furnace gas to a temperature approaching the freezing point of water whereby moisture in the furnace gas is condensed and removed from the furnace gas, a pump situated after said cooling means for pumping said gas to the measuring instruments, and a water separator situated after said pump, said water separator including a fluid level sensor which, when the fluid level reaches it, automatically generates a signal which closes valve means to stop the flow of gas to said measuring instruments to prevent damage thereto.

11. The apparatus of claim 10 further including a second filter means located between said pump and said water separator.

12. A method of cleaning gas from a furnace before it is supplied to at least one measuring instrument for analysis thereof, said method including:
   (1) filtering said furnace gas to remove particulate matter;
   (2) cooling said furnace gas to near the freezing point of water to thereby condense any moisture in the furnace gas and thus remove it from the furnace gas as a liquid;
   (3) continuously collecting the water condensed during the cooling step; and
   (4) sensing when a predetermined amount of water has been collected and, when said predetermined amount of water has been collected, feeding pressurized gas through the filter to thereby reverse flush it.

13. The method of claim 12 further including permitting said furnace gas, after it is cooled, to continuously warm as it passes to and through the measuring instruments whereby the likelihood of condensation in said measuring instruments is substantially reduced.

14. An apparatus for automatically adjusting operating conditions in a furnace, said apparatus including:
   a. Means for removing furnace gas from said furnace;
   b. Means for cleaning said furnace gas, said means for cleaning including:
      (i) Filter means for removing particulate matter;
      (ii) Cooling means for removing moisture, said cooling means cooling the furnace gas to a temperature approaching the freezing point of water whereby moisture in the furnace gas is condensed and removed from the furnace gas;
   c. At least one measuring instrument for analyzing at least one property of the cleaned furnace gas, said measuring instrument being capable of emitting an electrical signal in relation to the analysis of the measured property;
   d. Means for receiving said signal from the measuring instrument and adjusting furnace operating conditions in response thereto;
   e. Means for transporting the water condensed in the cooling means to a separate container; and
   f. A water level sensor in said separate container which is activated upon the water level reaching a predetermined height in said separate container and activation of the water level indicator automatically generating a signal operative to close valve means which shut off the furnace gas flow to the measuring instruments and open other valve means to permit the supply of a pressurized gas to said separate container and to said filter means to thereby reduce the water level in said separate container and to clean said filter means by reverse flushing thereof.

15. The apparatus of claim 14 further including means for controlling the rate of reduction of water level in said separate container.

16. The apparatus of claim 14 wherein said separate container further includes a low level water indicator which, when activated, generates a signal operative to close said other valve means to shut off the supply of pressurized gas to said separate container and said filter means and to reopen said valve means to again permit furnace gas flow to said measuring instruments.

17. The apparatus of claim 14 wherein the cooling means is a vortex cooler.

18. The apparatus of claim 17 wherein the coolant for the vortex cooler is compressed air and the same supply of compressed air is used as the said pressurized gas.

19. The apparatus of claim 14 further including means for monitoring the temperature in said cooling means and adjusting the temperature in said cooling means to a predetermined level approaching the freezing point of water.

20. The apparatus of claim 14 wherein said measuring instruments include instruments for measuring at least carbon dioxide and oxygen levels in said furnace gas.

21. Apparatus for cleaning of industrial off-gasses, said apparatus being situated between a furnace generating said gasses and instruments for analysis of said off-gasses, said cleaning apparatus comprising:
   (a) a ceramic heat filter through which the off-gasses pass, said ceramic heat filter including an electric bulb for heating thereof;
   (b) a cooler operative to cool the off-gasses to a temperature of about 2° C. after they leave the ceramic heat filter;
   (c) a container positioned below said cooler, said container being in fluid communication with said cooler whereby water condensed from said off-gasses in said cooler is transported to said container;
   (d) a sensor in said cooler operative to determine when water in said container has reached an upper and a lower limit;
   (e) said sensor generating a first signal when water reaches said upper limit, said first signal being operative to close valve means thus preventing the passage of gas from said cooler to said instruments for analysis of said off-gasses;
   (f) said first signal also opening other valve means to permit egress of water from said container and to permit reverse flushing of said ceramic heat filter;
   (g) means for generating compressed air;
   (h) conduit means for transporting said compressed air to said water container and said ceramic heat filter for reverse flushing thereof;
   (i) said sensor generating a second signal when the water level in the container reaches said lower limit; and
   (j) said second signal being operative to reopen said valve means and to close said other valve means whereby said off-gasses can again flow from said furnace to said instruments for analysis.

* * * * *